United States Patent [19]

Scialpi

[11] Patent Number: 4,670,247
[45] Date of Patent: Jun. 2, 1987

[54] PROCESS FOR PREPARING FAT-SOLUBLE VITAMIN ACTIVE BEADLETS

[75] Inventor: Leonard J. Scialpi, Andover, N.J.

[73] Assignee: Hoffman-LaRoche Inc., Nutley, N.J.

[21] Appl. No.: 844,258

[22] Filed: Mar. 24, 1986

Related U.S. Application Data

[63] Continuation of Ser. No. 510,505, Jul. 5, 1983, abandoned.

[51] Int. Cl.$^4$ .......................... A61J 3/00; A61K 9/36; A61K 9/64; A61K 9/40
[52] U.S. Cl. .................................... 424/484; 514/167; 514/458; 514/548; 514/681; 514/725; 514/960
[58] Field of Search ...................... 424/16, 35, 36, 37, 424/19; 514/948, 905, 167, 458, 548, 681, 725, 960

[56] References Cited

U.S. PATENT DOCUMENTS

| | | | |
|---|---|---|---|
| 2,613,206 | 10/1952 | Caldwell | 260/233.5 |
| 2,756,177 | 7/1956 | Cannalonga | 424/284 |
| 3,067,105 | 12/1962 | Ratish et al. | 424/237 |
| 3,207,666 | 7/1965 | Houtgraaf et al. | 424/236 |
| 3,445,563 | 5/1969 | Clegg et al. | 424/236 |
| 3,574,820 | 4/1971 | Johnson et al. | 424/37 |
| 3,786,123 | 1/1974 | Katzen | 424/236 |
| 4,138,362 | 2/1979 | Vassiliades et al. | 424/37 |
| 4,169,804 | 10/1979 | Yapel, Jr. | 424/36 |
| 4,273,672 | 6/1981 | Vassiliades | 424/37 |

OTHER PUBLICATIONS

Bender, in *The Importance of Vitamins to Human Health*, T. G. Taylor, ed., MTP Press Ltd., Lancaster, p. 112, (1979).

Kutsky, *Handbook of Vitamins and Hormones*, Van Nostrand Reinhold Co., New York, pp. 9, 25, (1973).

*Primary Examiner*—Douglas W. Robinson
*Attorney, Agent, or Firm*—Jon S. Saxe; George M. Gould; Norman C. Dulak

[57] ABSTRACT

A process is described for the preparation of fat-soluble vitamin active beadlet compositions which exhibit superior stability when exposed to the feed pelleting process. The process includes forming an aqueous emulsion of a fat-soluble vitamin-active material, gelatin, and a sugar converting the emulsion to dry particulate form containing the non-aqueous constituents of the emulsion and heat treating the resulting product to form water insoluble beadlets.

4 Claims, No Drawings

PROCESS FOR PREPARING FAT-SOLUBLE VITAMIN ACTIVE BEADLETS

This application is a continuation of application Ser. No. 510,505, filed July 5, 1983, now abandoned.

BACKGROUND OF THE INVENTION

The prior art discloses fat-soluble vitamin powder compositions which are useful for administration as such and also for the formation of pharmaceutical dosage forms, for example, tablets, capsules, powders, and the like; and for the preparation of animal feeds. U.S. Pat. No. 2,756,177 discloses a process for preparing dry, free-flowing powders by forming an emulsion containing a vitamin-active material, water, gelatin, and/or gum acacia and a sugar; converting the emulsions to droplets; collecting the individual droplets in a mass of starchy powder in such a manner that the vitamin-active particles formed from the droplets are kept separated from each other until their particulate form is established; and separating the vitamin-active particles from the starchy collecting powder. The vitamin-containing powder prepared according to the above process is water soluble and exhibits satisfactory stability properties for most uses; however, the material does have problems withstanding the stresses of pelletizing when used for the fortification of animal feeds. The vitamin containing material tends to lose its physical integrity under the temperature, moisture, and pressure conditions of the feed pelleting process and results in a loss of the physical integrity of the product thereby compromising the stability of the fat-soluble vitamin.

It is an important object of the invention to provide a vitamin-active preparation in the form of beadlets characterized by high stability and potency. A further object is to provide a vitamin-active beadlet which will withstand the temperature, moisture, and pressure of the feed pelleting process without losing their physical integrity. A still further object is to provide a vitamin-active preparation which is water insoluble, maintains bioavailability, and exhibits superior stability when pelletized.

DETAILED DESCRIPTION OF THE INVENTION

The present invention relates to a vitamin-active preparation in the form of a water insoluble beadlet comprising the steps of forming an emulsion containing the vitamin-active material, water, gelatin, and a sugar; converting the emulsion to droplets; collecting the individual droplets in a mass of starchy powder in such a manner that the vitamin-active particles from the droplets are kept separated from each other until their particulate is permanently established; separating the vitamin-active particles from the starchy collecting powder, and heat treating the particles at a temperature of from about 90° C. to about 180° C.

In accordance with the process of the invention, the heat treatment step insolubilizes the gelatin matrix of the beadlet by a reaction between the carbonyl group of the sugar with the free amino moieties of the gelatin molecule. The resulting beadlets are water-insoluble and exhibit increased stability to the stresses of feed pelleting. The crosslinking process utilizes the ingredients employed in making the beadlet and does not require addition of a crosslinking reagent or additive to the composition.

Fat-soluble vitamin-active materials which can be used in the practice of this invention are vitamin-bearing oils, provitamins, and pure or substantially pure vitamins, both natural and synthetic, or chemical derivatives thereof and mixtures thereof. Of particular interest is the preparation of beadlets containing vitamin A-active materials, more particularly, vitamin A acetate or vitamin A palmitate, but it is also contemplated to encompass beadlets containing any fat-soluble vitamin-active material, for example, vitamins A, D, E, or K, a carotenoid such as $\beta$-carotene, and the like, or mixtures of such materials when prepared according to the process of this invention.

In addition, this process is applicable to the preparation of fat soluble drugs. The final product in this case would not be soluble in the stomach but is soluble in intestinal juice.

The first step of the process according to the invention comprises emulsifying the fat-soluble vitamin-active material with water, gelatin, and a sugar.

Any gelatin which has a bloom in the range of practically zero to about 300 can be employed in the practice of the present invention. Both Type A and Type B gelatin can be employed.

Among the sugars used in forming the emulsions employed herein are fructose, glucose, lactose, maltose, and invert sugar (mixture of glucose and fructose). In addition, high fructose corn syrups (mixtures of fructose and dextrose) can also be employed in the practice of the invention. If sucrose were used, the beadlet might also be insoluble but would require higher temperature/longer time, resulting in vitamin A degradation and would most likely have been insolubilized through another mechanism (gel dehydration, etc.).

Small quantities of other ingredients including antioxidants, such as, butylated hydroxy anisole, butylated hydroxy toluene (BHT), ethoxyquin(6-ethoxy-1,2-dihydro-2,2,4-trimethyl-quinoline), and the like; humectants, such as glycerin, sorbitol, polyethylene glycols, propylene glycol, and the like; emulsifiers, such as lecithin; extenders and solubilizers; coloring agents; can also be incorporated in the emulsions of this invention.

The preparation of the vitamin-containing emulsion can be effected by methods which will be apparent to those skilled in the art. As an example of a method which we have found satisfactory, we mention the following: The gelatin dissolved in water with the aid of moderate heating, and the vitamin-active substance is then dispersed or emulsified in the solution of the gelatin. The sugar, as well as any ingredients, can be introduced into the mixture either before or after adding the vitamin-active material. The mixture is agitated until all dispersoids are uniformly distributed; if necessary, by passing the mixture through a homogenizer.

The starchy powder used in the process to collect the droplets of emulsion can consist entirely of a starch and/or a starch chemically modified so as to impart to it in greater degree those characteristics found to be desirable in the collecting powder, as recited hereinbelow. The collecting powder can also contain, in addition to the starch and/or modified starch, minor amounts of lubricants and other modifiers, such as talc, silicic acid, flours, hydrogenated fats and metal salts of higher fatty acids, for example, calcium stearate. The collecting powder should possess the following characteristics: it should be substantially insoluble in cold water and, moreover, should be resistant to wetting by water; it should have an appreciable capacity to absorb and/or adsorb water; and it should be free-flowing. An important characterisic of the collecting powder is that its moisture content must be below about 10 percent. The desired moisture content can be easily attained by drying the commercially available starches or chemically modified starches.

A preferred collecting powder consists substantially entirely of a starch modified to contain hydrophobic groups so as to possess the properties of free-flow and resistance to water-wetting to a higher degree than unmodified starch. Starch derivatives of this type, more particularly starch esters, are disclosed in U.S. Pat. No. 2,613,206. A free-flowing starch ester, resistant to water-wetting, available commercially under the designation "Dry-Flo" and distributed by National Starch Products, Inc., New York, N.Y., has been found convenient to use as the specific starch ester for a preferred embodiment of the invention. As indicated, the "Dry-Flo" must be dried, to reduce its moisture content before use.

The introduction of droplets of the vitamin-containing emulsion into the collecting powder can likewise be effected by various methods which will suggest themselves to those skilled in the art. An important concept in the practice of this step of our invention is that of keeping the vitamin-active particles formed in the collecting powder by the emulsion droplets separated from each other for a long enough time that they will "set-up." That is, the vitamin-active particles should be kept separated from each other until their particulate form is permanently established, by loss of water, i.e., to such an extent that they will not agglomerate or coalesce during the most severe conditions of further processing, e.g., when the particles are spread out to dry on trays at about 45° C. The conversion of emulsion droplets to "set up" particles can obviously be attained in various ways. For example, the emulsion droplets can be let fall by a moving nozzle upon a stationary layer of collecting powder at such a space interval that the droplets do not run together. Or, the collecting powder can be presented as a moving layer (e.g., as on a conveyer belt) below a fixed nozzle adjusted to let the droplets fall at a rate such that the droplets do not run together in the powder. Still another method is represented by the spraying of emulsion droplets into an agitated mass of collecting powder, as in a tumbler or in a vessel provided with a stirrer. The particular method employed is not of the essence of the invention. However, a preferred method comprises introducing a spray of emulsion droplets into an agitated cloud or suspension in air of the particles of collecting powder. As illustrative of this latter, a method which has been found useful in quantity production comprises forcing the emulsion through a revolving spray head, having several rows of tiny orifices therein, into a suspension in air of the powdered starchy material, contained in and agitated by a revolving cylindrical drum, the drum and the spray head rotating in opposite directions so that the cloud or suspension of the starchy powder in air is swirling in a sense of rotation opposite to the entering emulsion spray. It has been found to be advantageous to include pulverized dry ice or liquid carbon dioxide in the starch bed in order to fluidize and cool the starch to less than 10° C.

The separation of the vitamin-active particles from the collecting powder can be accomplished by operations which are conventional per se. It has been found convenient simply to feed the mixture of powder and vitamin-active particles to a shaking screen of a size selected to retain the vitamin-active particles while passing the collecting powder. It is advantageous to so adjust the conditions under which the droplets of emulsion are formed, e.g., size of nozzle orifice, viscosity and percentage water content of emulsion, etc., as will be obvious to those skilled in the art; that the final size of the vitamin-active particles is substantially entirely in the range which will pass through a 10-mesh screen and be retained upon a 200-mesh screen. A preferred size of vitamin-active particle for animal feed formulations is in the range which will pass through a 20-mesh screen and be retained upon a 170-mesh screen. The starchy collecting powder is selected to have a smaller particle size; it being understood that for any desired size range of vitamin-active particle, the particles of collecting powder employed will be selected in a range of appreciably smaller size. A preferred size for collecting powder is in the range which will pass substantially entirely through a 200-mesh screen.

The particles containing vitamin-active material formed in the collecting powder by droplets of emulsion should be dried to a moisture content of less than 10% and preferably between about 4–6 percent. The particles can be dried by various methods. The collecting powder itself effects a certain measure of drying insofar as it absorbs and adsorbs part of the water contained in the drops of emulsion, and this drying initiates the "setting up" phenomenon (i.e., the conversion of the droplet to a particle which will retain its particulate form even upon contact with other similar particles during further processing). The remaining water can be removed by various methods. For example, one can dry the entire mass, i.e., the collecting powder containing therein the vitamin-active particles, and then separate the collecting powder from the dried vitamin-active particles. It is preferable to separate the vitamin-active particles shortly after they are formed in the powder, i.e., after their particulate form has been permanently established but before they are completely dry; and then to dry the vitamin-active particles substantially free of collecting powder; for example, by exposing them to air at room temperature, or by moderate heating in an oven at 37° or 45° C.

Heat treatment of the above vitamin-active beadlet composition at a temperature of from about 90° C. for 2 hours to about 180° C. for less than 1 minute, and preferably from about 105° C. for 60 minutes to 150° C. for 10 minutes, results in crosslinking of the gelatin sugar matrix. Assays of beadlets prepared by the method of this invention indicate no loss of vitamin A on processing; in fact, potency increased in proportion to the loss of residual beadlet moisture. The reaction involves the carbonyl of the sugar molecule with the free amino moieties of the gelatin molecule. Vitamin-active beadlets crosslinked by this technique are insoluble in boiling water and possess better stability to the conditions utilized in pelletizing the beadlets for animal feed compositions.

Beadlets crosslinked by this technique are insoluble in boiling water and exhibit the properties of an enteric coating; specifically, one with little or no dissolution in gastric fluid ($pH \sim 1$) but completely soluble in intestinal fluid ($pH \sim 8$). These characteristics would benefit any substance (vitamin, drug, carotenoid, etc.) which is degraded by the acid environment of the stomach and/or is better absorbed in the intestinal tract. The net effect of such a modification is improved bioavailability in the target species.

An important advantage of this crosslinking approach is that the beadlets maintain their initial dissolution profile with storage. Aldehyde (e.g., formaldehyde, glyceraldehyde) or ketone crosslinks tend to continue polymerizing with time resulting in decreased bioavailability. USP simulated gastric and intestinal fluids were used to determine in vitro dissolution of these preparations. Selected formulations were evaluated in preliminary bioavailability studies by the chick liver storage method using a single dose level (10,000 IU/Kg feed). The results shown below indicate the heat hardened insoluble beadlets have excellent bioavailability when compared to soluble beadlets of the same vitamin composition (taken as 100%).

|  | Avg. % Deposition | Relative Deposition |
|---|---|---|
| Example 2 | 39.8 | 107 |
| Example 4 | 40.3 | 108 |
| Example 7B | 42.7 | 115 |

The fat-soluble vitamin powder compositions of the present invention comprise 20–30%, preferably 23–28%, by weight of vitamin A active material; 2–20%, preferably 5–12%, by weight of a reducing sugar; 35–45%, preferably 36–40%, by weight of gelatin; 5–20%, preferably 10–15%, by weight of hydrophobic starch; 5–13%, preferably 6–10%, by weight of an antioxidant; 0–15%, preferably 5–10%, by weight of a humectant.

The process of this invention is further illustrated by reference to the following Examples.

EXAMPLE 1

246 gm of gelatin, approximately 200 Bloom, were dissolved in 300 gm of distilled water by heating to about 65° C. with stirring. 45 gm of High Fructose Corn Syrup (55%) and 36 gm of glycerin were added to the gelatin solution with stirring. 150 gm of crystalline vitamin A acetate, 2.9 million IU/gm vitamin A activity, previously melted with 43 gm of ethoxyquin (EMQ) at a temperature of about 65° C. was slowly added to the gelatin/sugar solution and homogenized until well dispersed. An additional 275 to 300 ml distilled H₂O previously heated to about 55° C. was added to the emulsion while stirring to provide a viscosity suitable for spraying. The emulsion was loaded into an apparatus provided with a revolving spray head and a counter-rotating drum as above described. The drum was charged with approximately 7 kg "Dry Flo", previously dried to a moisture content of 3–5%, and 3.5 kg pulverized dry ice. The emulsion was sprayed into the "Dry Flo" bed and the mixture of starch and vitamin beadlets allowed to stand overnight before being screened through a 170-mesh screen. The beadlets retained upon the screen were collected, spread out on drying trays and dried in an oven at 37° C. for 7 hours to a moisture content of 4%. The beadlets were crosslinked by heating for 10 minutes on pre-heated stainless steel trays in an electric oven set to a temperature of 150° C. The beadlets thus obtained were insoluble in water, had a particle size of 20–170 mesh, a moisture content of 1% and assayed 687,000 IU vitamin A activity/gm.

EXAMPLE 2

In the manner described in Example 1, an emulsion was prepared from the following ingredients:

|  | gms |
|---|---|
| Vitamin A Acetate, crystalline, 2.9 million IU/gm | 156 |
| EMQ | 57 |
| Lactose U.S.P. | 42 |
| Glycerin | 42 |
| Low Bloom Gelatin | 240 |
| (Type A, apx. 100 Bloom) | |
| Distilled Water: for Emulsion | 240 |
| for Spraying | q.s. |

The emulsion thus obtained was formed into particles by means of the same apparatus and in the same manner as described in Example 1.

The beadlets were crosslinked by heating for 15 minutes at 150° C. The beadlets thus obtained have an average size substantially as in Example 1 and assayed 674,000 IU/gm.

EXAMPLE 3

In the manner described in Example 1, an emulsion was prepared from the following ingredients:

|  | gms |
|---|---|
| Vitamin A Acetate, crystalline 2.9 million IU/gm | 168 |
| BHT | 60 |
| Invert Sugar (Total) | 51 |
| Glycerin | 39 |
| Low Bloom Gelatin | 240 |
| (Type B, apx. 75 Bloom) | |
| Distilled Water (for Emulsion) | 240 |

The emulsion thus obtained was formed into particles by means of the same apparatus and in the same manner as described in Example 1.

The beadlets were crosslinked by heating for 10 minutes at 150° C. The beadlets thus obtained have an average size substantially as in Example 1 and assayed 690,000 IU/gm.

EXAMPLE 4

In the manner described in Example 1, an emulsion was prepared from the following ingredients:

|  | gms |
|---|---|
| Vitamin A Acetate, crystalline 2.9 million IU/gm | 156 |
| EMQ | 57 |
| Glucose | 42 |
| Glycerin | 42 |
| Low Bloom Gelatin | 240 |
| (Type A, apx. 100 Bloom) | |
| Distilled Water (for Emulsion) | 240 |

The emulsion thus obtained was formed into particles by means of the same apparatus and in the same manner as described in Example 1.

The beadlets were crosslinked by heating for 30 minutes at 135° C. The beadlets thus obtained have an average size substantially as in Example 1 and assayed 699,000 IU/gm.

EXAMPLE 5

In the manner described in Example 1, an emulsion was prepared from the following ingredients:

|  | gms |
|---|---|
| Vitamin A Acetate, crystalline 2.9 million IU/gm | 156 |
| EMQ | 57 |
| Crystalline Fructose | 54 |
| Glycerin | 54 |
| Low Bloom Gelatin (Type A, apx. 100 Bloom) | 216 |
| Distilled Water (for Emulsion) | 220 |

Adjusted emulsion to pH 8.2 with 20% w/w sodium hydroxide solution.

The emulsion thus obtained was formed into particles by means of the same apparatus and in the same manner as described in Example 1.

The beadlets were crosslinked by heating for 60 minutes at 105° C. The beadlets thus obtained have an average size substantially as in Example 1 and assayed 686,000 IU/gm.

EXAMPLE 6

In the manner described in Example 1, an emulsion was prepared from the following ingredients:

|  | gms |
|---|---|
| Vitamin A acetate, crystalline 2.9 million IU/gm | 150 |
| EMQ | 43 |
| High Fructose Corn Syrup (55%) | 92 |
| Gelatin (apx. 200 Bloom) | 246 |
| Distilled Water (for Emulsion) | 300 |

The emulsion thus obtained was formed into particles by means of the same apparatus in the same manner as described in Example 1.

The beadlets were crosslinked by heating for 10 minutes at 150° C. The beadlets thus obtained have an average size substantially as in Example 1 and assayed 684,000 IU/gm.

EXAMPLE 7

In the manner described in Example 1, an emulsion was prepared from the following ingredients:

|  | gms |
|---|---|
| Vitamin A Acetate, crystalline 2.9 million IU/gm | 156 |
| EMQ | 57 |
| Glucose | 42 |
| Glycerin | 42 |
| Low Bloom Gelatin (Type A, apx. 100 Bloom) | 240 |
| Distilled Water (for Emulsion) | 240 |

The emulsion thus obtained was formed into particles by means of the same apparatus and in the same manner as described in Example 1.

The beadlets were divided into three portions, and the portions were crosslinked using the following conditions:

|  | Heat Treatment | Assay (IU/gm) |
|---|---|---|
| 7A | 150° C. for 10 minutes | 712,000 |
| 7B | 135° C. for 25 minutes | 690,000 |
| 7C | 120° C. for 50 minutes | 712,000 |

EXAMPLE 8

In the manner described in Example 1, an emulsion was prepared from the following ingredients:

|  | gms |
|---|---|
| Vitamin A Acetate, crystalline 2.9 million IU/gm | 156 |
| EMQ | 57 |
| Invert Sugar (Total) | 55 |
| Glycerin | 42 |
| Hydrolyzed Gelatin | 270 |
| Distilled Water (for Emulsion) | 270 |

The emulsion thus obtained was formed into particles by means of the same apparatus and in the same manner as described in Example 1.

The beadlets were crosslinked by heating for 10 minutes at 150° C. The beadlets thus obtained have an average size substantially as in Example 1 and assayed 701,000 IU/gm.

EXAMPLE 9

In the manner described in Example 1, an emulsion was prepared from the following ingredients:

|  | gms |
|---|---|
| Vitamin A Acetate, crystalline 2.9 million IU/gm | 150 |
| EMQ | 43 |
| High Fructose Corn Syrup (55%) | 45 |
| Propylene Glycol | 36 |
| Gelatin (apx. 200 Bloom) | 246 |
| Distilled Water (for Emulsion) | 300 |

The emulsion thus obtained was formed into particles by means of the same apparatus and in the same manner as described in Example 1.

The beadlets were crosslinked by heating for 10 minutes at 150° C. The beadlets thus obtained have an average size substantially as in Example 1 and assayed 694,000 IU/gm.

I claim:

1. In the process of preparing a fat-soluble vitamin active particulate composition which includes forming an aqueous emulsion of a fat-soluble vitamin-active material selected from the group consisting of vitamin A, D, E, K and derivatives thereof and a protective colloid comprising gelatin and a reducing sugar and further converting said emulsion to a dry particulate form containing the non-aqueous constituents of said emulsion, the improvement which comprises cross-linking the dry particulate form by heat treating said particulate form obtained from said step (2) at from about 90° C. for 2 hours to about 180° C. for less than a minute, whereby such heat treatment insolubilizes the gelatin matrix of the beadlet by a reaction between the carbonyl group of the sugar with the free amino moieties of the gelatin molecule to form water insoluble beadlets.

2. The process according to claim 1 wherein the particulate form is heated at from about 105° C. for 60 minutes to about 150° C. for 10 minutes.

3. A fat-soluble vitamin active particulate composition prepared according to the process of claim 1.

4. The fat-soluble vitamin active particulate composition of claim 4 comprising 20-30% of a vitamin, 2-20% of a reducing sugar, 35-45% of a gelatin, 5-20% of a hydrophobic starch, 5-13% of an antioxidant and 0-15% of a humectant, wherein the range ingredients are in percent by weight.

* * * * *